United States Patent [19]

Roeraade

[11] 4,424,127
[45] Jan. 3, 1984

[54] COLUMN FOR LIQUID AND GAS CHROMATOGRAPHY

[76] Inventor: Johan Roeraade, Sågvägen 4, Tumba, Sweden, 147 00

[21] Appl. No.: 317,901

[22] PCT Filed: Mar. 6, 1980

[86] PCT No.: PCT/SE81/00067
§ 371 Date: Nov. 2, 1981
§ 102(e) Date: Nov. 2, 1981

[87] PCT Pub. No.: WO81/02527
PCT Pub. Date: Sep. 17, 1981

[30] Foreign Application Priority Data

Mar. 7, 1980 [SE] Sweden .................... 8001821

[51] Int. Cl.³ ............................. B01D 15/08
[52] U.S. Cl. ..................... 210/198.2; 55/386
[58] Field of Search ........... 210/198.2; 55/386, 158, 55/67

[56] References Cited

U.S. PATENT DOCUMENTS

| 3,442,002 | 5/1969 | Geary, Jr. et al. | 55/158 X |
| 3,570,673 | 3/1971 | Dutz et al. | 210/198.2 |
| 4,031,012 | 6/1977 | Gics | 55/158 X |
| 4,293,415 | 10/1981 | Bente et al. | 210/198.2 |

FOREIGN PATENT DOCUMENTS

| 1598214 | 12/1969 | Fed. Rep. of Germany . |
| 2821105 | 11/1979 | Fed. Rep. of Germany . |
| 374210 | 2/1975 | Sweden . |
| 375156 | 4/1975 | Sweden . |

Primary Examiner—John Adee
Attorney, Agent, or Firm—Burns, Doane, Swecker & Mathis

[57] ABSTRACT

Column for carrying out gas or liquid chromatography comprising several capillaries coupled in parallel the capillaries being arranged side by side or woven or pleated together in the form of a flat band-like device, whereby the column can be bent and rolled up without tensions arising in same.

14 Claims, 6 Drawing Figures

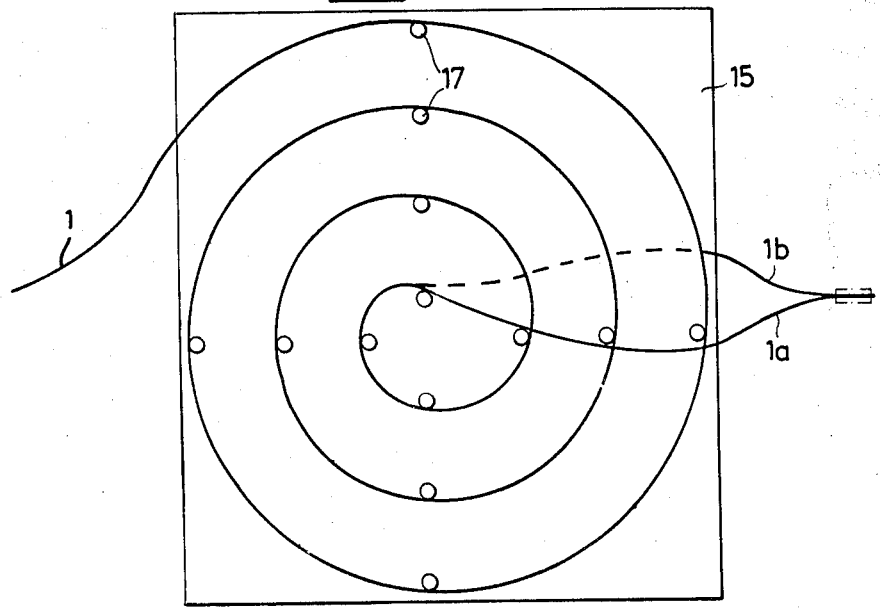

COLUMN FOR LIQUID AND GAS CHROMATOGRAPHY

The present invention relates to a column for performing liquid and gas chromatography, particularly the latter, comprising a plurality of capillaries coupled in parallel.

Gas chromatography based on the use of single capillaries as a column is often used to a large extent in analytic chemistry. The different advantages and effects which can be obtained by such capillary columns are extensively described in the literature, for example Kaiser, R.E.: Chromatographie in der Gasphase, third ed., Vol. 2, Bibliographisches Institut, Mannheim, 1975; Ettre, L.S.: Open Tubular Columns in Gas Chromatography, Plenum Press, New York, 1965.

The primary advantage of using a capillary column is the good separation effect that can be obtained. Thus, it is generally known that the smaller the interior diameter of the column the better the dissolution, i.e. the separation of the components of the gas mixture. However, capillary columns are subject to the obvious disadvantage that their capacity is strongly delimited, which necessitates the use of particular sample injecting devices and very sensitive detectors.

The use of several capillary columns with as identical properties as possible and coupled in parallel could result in elimination of the disadvantage residing in the limited capacity of the capillary column. By using a larger number of capillary columns coupled in parallel it would thus be possible to separate and prepare substances in a pure form in large quantities while maintaining the ability of the single capillary column of chromatographic dissolution.

However, hitherto proposed multicapillary column constructions have not been found to be practically useful, mainly in view of the fact that it has been found to be difficult to provide for a column composed of several capillaries coupled in parallel wherein in practical operation the individual capillaries show a somewhat identically similar behaviour. The differences that may arise between the individual capillaries in the composite column can consist in deformation of the capillaries in different degrees depending on the position in the column structure, arising temperature gradients over the cross section of the column, etc. The first one of said differences between the individual capillaries in the column can be wholly devastating for the operational characteristic in view of the fact that the linear flow through a capillary tube is proportional to the fourth power of the inner diameter of the tube in accordance with Poiseuille's equation: (modified)

$$F = (\pi d^4 \cdot dp)/(128\eta dL)$$

wherein
d = tube diameter
dp = pressure differential
$\eta$ = gas viscosity
L = length of tube
F = gas flow (ml/min.)

For longer tubes having a greater pressure drop also the compressibility of the gas must be introduced as a factor but this does not change the dependence of the gas flow of the fourth power of the diameter.

Another essential disadvantage of proposed constructions based on the multi-capillary column is the relatively large thermal mass of the column, whereby it is not possible rapidly to change the temperature of the column without causing radial temperature gradients which result in different separation rates of the different capillaries which results in loss of the dissolution ability of the multicolumn.

The present invention has for its purpose to provide a column for carrying out gas chromatography and wholly or partly avoiding the above disadvantages. For this object the invention provides for a column wherein the capillaries are arranged side by side or woven or pleated together in the form of a flat band-like device. By arranging the column in this manner the essential advantages are obtained residing in the fact that the column can be bent and rolled up without resulting tensions and deformations in same.

In its simplest form the column according to the present invention consists of capillaries arranged side by side, the capillaries preferably in some suitable manner being held together mechanically, at least laterally. The simplest way of keeping the capillaries together consists in baking same into some suitable binding material, for example a hardenable plastic.

In an alternative embodiment of the column according to the invention the capillaries are held side by side by gluing to a support, for example a plastic foil, or are arranged between two layers of for example plastic and are fixed by gluing to the two layers.

In the column according to the invention the capillaries may also be anchored mechanically in another manner, for example by lateral threads arranged in zigzag in relation to the capillaries. It is also practically fully conceivable to provide for mechanical anchorage of the capillaries to each other by weaving or pleating the individual capillaries together to form a flat woven or pleated product.

At both ends of the column according to the invention the capillaries are manifolded in a suitable manner for supply of carrier gas for chromatography and for discharge of separated products. In this case it is suitable, at least at one end of the column, to leave the capillaries free and separate from each other over a part of their lengths to enable trimming, which is further explained below, and to facilitate manifolding the capillaries to a unit.

A suitable capillary tube material is a flexible strong material and preferably silica capillaries are used which can be made with very thin walls and with a very small cross section diameter, down to about 0.1 mm or even less. In order to impart the necessary mechanical strength to the silica capillaries it is suitable to coat same with a thin layer of polymer, for example silicon or polyimide or of metal. An alternative conceivable material for the manufacture of the capillary tubes is steel or other metal or glass.

Assuming that flexibility can be maintained a few flat band-like devices can be positioned on top of each other, but an upper limit would seem to exist at 3-4 capillary layers arranged on top of each other. No upper limit as how many capillaries can be arranged side by side exists, since the column can be given any width with maintained flexibility and thus maintained uniform capillary characteristic. Since with today's techniques silica capillaries can be made which have a very small diameter, one may easily prepare a multicapillary column containing 100 capillaries laterally arranged and with a lateral dimension of less than 5 cm.

In the following the invention will be described by examples of embodiments in connection with the appended drawings, wherein:

FIG. 4 shows a cross-section through yet another embodiment of the column of the invention;

FIG. 5 shows another modified embodiment of the column of the invention; and

FIG. 6 shows diagrammatically a device for rolling up the column of the invention to the formation of a compact unit.

Figure 1:
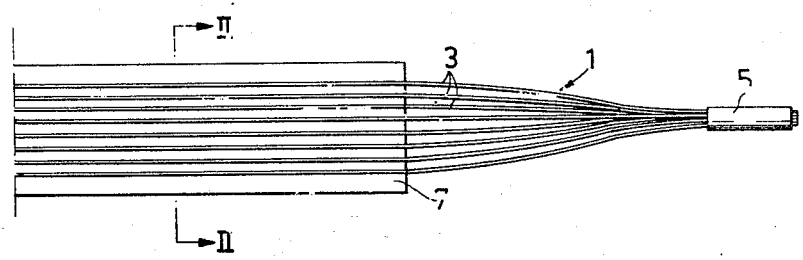
FIG. 1 shows diagrammatically one end of a column according to the invention.

In FIG. 1 there is shown diagrammatically a column made in accordance with the present invention and generally designated 1. The column is built up by capillaries 3 arranged side by side which capillaries at the ends thereof are baked together to a unit contained in a protecting sleeve 5.

Figure 2:
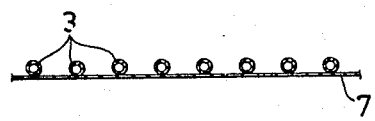
FIG. 2 shows a cross-section taken along line II—II in FIG. 1 and in enlargement.

In FIG. 2 there is shown a cross-section through the column taken along line II—II in FIG. 1, from which it is clear that the individual capillaries 3 are positioned side by side somewhat separated and glued to a support 7, for example a plastic film. The capillaries 3 extend beyond said plastic film 7 a distance which is clear from FIG. 1 for a purpose to be further explained below.

Figure 3:
FIG. 3 shows a cross-section through an alternative embodiment.

In FIG. 3 there is shown a modified embodiment wherein the capillaries 3 are arranged side by side immediately adjacent to each other and baked into a plastic mass 9. Baking in of the capillaries in a polymer can be done by feeding capillary tubes from individual spools through a bath of a non-cured polymer. As a starting material there may be used any suitable curing plastic, for example polyimide or silicon, and the band obtained which is not yet cured can be passed through an oven wherein polymerization takes place, the band being wound onto a drum until the desired length has been obtained.

In FIG. 4 there is shown a cross-section through yet another alternative embodiment of the column of the invention. In this embodiment capillaries 3 are arranged on a central support 11, for example plastic foil, on either sides either loosely positioned on the foil or fixed thereto by for example gluing, there being obtained a two-layer column with maintained good flexibility.

In FIG. 5 is shown a cross-section through an embodiment of the column of the invention, wherein the individual capillaries 3 are anchored mechanically side by side through lateral thread elements 13, for example of metal, plastic or other suitable material. The embodiment according to FIG. 5 can be said to be a woven product, wherein the capillaries 3 constitute the warp and thread elements 13 the weft.

It is also conceivable mechanically to attach the capillaries in relation to each other by some kind of plaiting, whereby it suitably is provided for the plait obtained being so flat that its thickness does not exceed a dimension corresponding to 2 to 3 capillary diameters.

FIG. 6 shows a device enabling winding up a long column so as to obtain it in a compact form. For gas chromatographic applications sometimes a length of column of up to about 200 meters may be desirable, and such column will, of course, in its extended form be clumsy to handle. However, the column construction in accordance with the invention enables assembling the column within a relatively small volume, such as illustrated in FIG. 6, with maintained low heat inertia.

In FIG. 6 the column 1 according to the invention is arranged wound up in the shape of a helix in a diagrammatically shown housing 15 containing guide pins 17 for arranging column 1 in a wound up form according to the figure. The outer left end is manifolded in the same manner as shown in FIG. 1 within a protecting sleeve 5, whereas the opposite end of column 1 in the centre of the helix is divided up into two parts 1a, 1b which, outside the casing 15, are brought together in another protecting sleeve 5.

Even while one using modern techniques could obtain capillary tubes with a very close tolerance with regard to its inner diameter it is, however, in view of Poiseuille's equation as referred to above essential to be capable of trimming the column with regard to the individual capillaries. Such trimming can be carried out before or after the interior coating of the capillary tubes with a stationary phase. If the trimming takes place before coating with stationary phase the flow resistance of the different tubes is suitably investigated by pressing a liquid, for example dichloromethane, into the capillaries and registering the positions of the liquid columns in the different capillaries immediately before leaving same. After thus establishing the positions in the tubes corresponding to the same effective column length the tubes can be severed at the positions marked and the ends levelled together while using the above mentioned free part of the capillaries.

Trimming of the capillaries can be performed also after coating with stationary phase. In this case each capillary is tested with regard to its chromatographic retention properties and adjustment in length can be calculated with Poiseuille's equation and the retention value obtained. Testing can be performed with for example a hydrocarbon, such as octane or nonane, at room temperature.

After the trimming procedure the ends of the capillaries are brought together to a bundle and the protecting sleeve 5 is moved on to the end which may then be permanently fixed by using for example a curing plastic.

The column according to the instant invention has essential advantages among which the following may be mentioned.

The construction allows rapid heating (temperature programming) in view of the small thermal mass in relation to exposed surface. Temperature gradients between the capillaries can be avoided, which is necessary in order that the dissolving ability of the individual capillaries shall be practically utilized parallel and synchronously.

The construction allows maintained mechanical flexibility of the column which can be wound up in the form of a spool without resulting in mechanical stresses so that the capillaries break or are mechanically released from each other.

When flexing the column in for example winding all capillaries in the column will maintain the same length.

The invention is not delimited to the above embodiments but can be modified in many respects within the scope of the appended patent claims.

I claim:

1. A gas or liquid chromatography column comprising a plurality of capillary tubes coupled in parallel, the capillary tubes being arranged in the form of a flat bandlike device, allowing the column to be bent and rolled up without tensions arising in same, the capillary tubes being adapted at a first end of the column to receive a supply of carrier fluid and at a second end of the column for discharge of separated products.

2. The column of claim 1, wherein the capillary tubes are laterally held together mechanically.

3. The column of claim 2, wherein the capillary tubes are held together by baking same into a binding material.

4. The column of claim 3, wherein the binding material is a thermosetting resin.

5. The column of claim 2, wherein the capillary tubes are held together by being glued side by side onto a support.

6. The column of claim 5 wherein the support is a plastic foil.

7. The column of claim 2, wherein the capillary tubes are held together by laterally extending threads.

8. The column of claim 2, wherein the capillary tubes are held together by weaving or pleating the individual capillary tubes together.

9. The column of claim 1, wherein the capillary tubes at least at one end of the column, are left free over part of their lengths to enable trimming and to facilitate manifolding the capillary tubes.

10. The column of claim 1, wherein the capillary tubes are made of silica.

11. The column of claim 10, wherein the capillary tubes are coated on their exterior with a thin polymer or metal layer.

12. The column of claim 1, wherein the capillary tubes are made from steel.

13. The column of claim 1, wherein a plurality of flat band-like devices are positioned on top of each other.

14. The column of claim 1, wherein the capillary tubes are arranged side by side.

* * * * *